United States Patent
Merk et al.

(10) Patent No.: US 9,393,380 B2
(45) Date of Patent: Jul. 19, 2016

(54) INTRODUCER SHEATH HAVING PROFILED REINFORCING MEMBER

(75) Inventors: James C. Merk, Terre Haute, IN (US); Melissa Dawn Baker, Ellettsville, IN (US); Mark J. Hiatt, Ellettsville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 823 days.

(21) Appl. No.: 13/569,487

(22) Filed: Aug. 8, 2012

(65) Prior Publication Data

US 2014/0046138 A1    Feb. 13, 2014

(51) Int. Cl.
A61F 2/95       (2013.01)
A61M 25/00     (2006.01)
B29L 31/00      (2006.01)
A61M 25/06     (2006.01)
B29C 53/12     (2006.01)

(52) U.S. Cl.
CPC ......... *A61M 25/0012* (2013.01); *A61M 25/005* (2013.01); *A61M 25/0662* (2013.01); *A61M 2025/0047* (2013.01); *A61M 2025/0059* (2013.01); *B29C 53/12* (2013.01); *B29L 2031/753* (2013.01)

(58) Field of Classification Search
CPC . A61M 25/005; A61M 25/0012; B29C 53/12
USPC ................. 604/524–527; 623/1.12
See application file for complete search history.

(56) References Cited

U.S. PATENT DOCUMENTS

| | | | |
|---|---|---|---|
| 5,380,304 A | 1/1995 | Parker | 604/282 |
| 5,769,830 A | 6/1998 | Parker | 604/282 |
| 5,792,124 A | 8/1998 | Horrigan et al. | 604/282 |
| 6,042,578 A * | 3/2000 | Dinh et al. | 604/527 |
| 6,152,912 A | 11/2000 | Jansen et al. | 604/526 |
| 6,206,753 B1 * | 3/2001 | Werner | 450/41 |
| 6,258,080 B1 | 7/2001 | Samson | 604/525 |
| 6,824,553 B1 | 11/2004 | Samson et al. | 606/192 |
| 6,939,337 B2 | 9/2005 | Parker et al. | 604/528 |
| 2001/0034514 A1 | 10/2001 | Parker | 604/525 |
| 2001/0044629 A1 * | 11/2001 | Stinson | A61B 17/12022 606/108 |
| 2005/0021002 A1 * | 1/2005 | Deckman et al. | 604/527 |
| 2007/0293930 A1 * | 12/2007 | Wang et al. | 623/1.11 |
| 2010/0030165 A1 * | 2/2010 | Takagi et al. | 604/265 |
| 2010/0049168 A1 | 2/2010 | Parker et al. | 604/527 |
| 2010/0057051 A1 | 3/2010 | Howat et al. | 604/526 |
| 2012/0078187 A1 * | 3/2012 | Delap | A61M 25/005 604/171 |

* cited by examiner

*Primary Examiner* — Sarah W Aleman
*Assistant Examiner* — Socrates L Boutsikaris
(74) *Attorney, Agent, or Firm* — Brinks Gilson & Lione

(57) ABSTRACT

An introducer sheath includes an inner liner having a passageway extending longitudinally therethrough, a coil positioned over the inner liner, and an outer jacket positioned over the liner and the coil. The outer jacket is bonded to the inner liner between the coil turns. The coil turns have a cross-section comprising opposing end portions, and a center portion disposed between the opposing end portions. The center portion has a thickness not exceeding about one-third of a thickness of the end portions for reducing a bending modulus of the coil, and the end portions have a generally curved outer surface. At least a distal end portion of the outer jacket has a durometer between about 70 and 90 on the Shore D scale.

13 Claims, 4 Drawing Sheets

US 9,393,380 B2

INTRODUCER SHEATH HAVING PROFILED REINFORCING MEMBER

BACKGROUND

1. Technical Field

This invention relates to the field of medical devices, and more particularly, to an introducer sheath having a reinforcing member profiled for enhancing the flexibility of the sheath.

2. Background Information

Numerous advances of considerable note have occurred in medical surgical techniques over the last few decades. Among the most significant advances has been the adoption, and now-routine performance, of a wide variety of minimally invasive procedures. When carrying out such procedures, access to a site of concern within a patient is achieved through a relatively small incision, into which a tubular device (such as a sheath) is inserted or introduced. The sheath keeps the incision open while permitting access to the target site via the interior (i.e., lumen) of the sheath. Non-limiting examples of such devices include introducer sheaths, guide catheters, and like devices (devices collectively referred to herein as "sheaths" or "introducer sheaths").

Body passageways in which medical interventional devices, such as stents, are now commonly introduced include the esophagus, trachea, colon, biliary tract, urinary tract, and vascular system, among other locations within the body. When placing a medical interventional device in a passageway, communication with the passageway is typically attained by initially inserting the distal end of the introducer sheath into the body passageway. Since the introducer sheath must often traverse tortuous passageways to reach the target site, the sheath often includes a coil reinforcement to enhance the flexibility of the sheath, and thereby, facilitate passage of the sheath through the passageway without kinking. Examples of introducer sheaths of this type are described in U.S. Pat. No. 5,380,304, and U.S. Pat. Publ. No. 2001/0034514, both incorporated by reference herein, The sheaths described in these patent documents include a lubricious inner liner and a helical coil fitted over the liner. The coil is typically formed from flat wire, i.e., wire having a substantially rectangular cross-section. Utilizing a flat wire coil enables the sheath to maintain the smallest possible wall diameter, while at the same time providing suitable radial support to the sheath. An outer tube is formed of a composition, such as a polyether block amide or a polyamide (nylon), that provides sufficient flexibility to the sheath so that it can bend along the tortuous passageways.

The medical interventional device, such as an expandable stent, etc., is delivered to the target site from a lumen in the introducer sheath. Typically, the device is deployed at the target site by withdrawing the introducer sheath from around the stent while the stent is in a constricted condition. An inner catheter may be provided in the sheath lumen for preventing the stent from withdrawing with the sheath. In an alternative arrangement, the constricted stent may be pushed from the distal end of the sheath by a pusher mechanism positioned in the sheath lumen. In either technique, upon deployment from the sheath at the target site, the device expands to the diameter of the surrounding body passageway.

Deployment of expandable medical interventional devices, such as stents, in this manner is now a routine practice, and such deployment is often carried out with only a minimum of complications, if any. This is particularly true when such devices have a relatively short length (e.g., less than about 80 mm) and/or a relatively modest outer diameter. However, as medical technology has progressed, stents and other interventional devices having longer lengths (e.g., about 100 to 300 mm or more) and/or having outer coatings, coverings, etc., that increase the effective outer diameter of the stent have become more common. When such stents are placed in a sheath lumen for delivery to the target site, the greater length and/or outer diameter of the stent increases the deployment forces necessary to extract the stent from the sheath when compared to shorter and/or lesser diameter stents. This increase in deployment forces is due primarily to the increased radially outwardly-directed forces exerted by the longer and/or greater diameter stents on the interior wall of the sheath.

In this event, an introducer sheath having a coiled reinforcement as described above has a tendency to stretch longitudinally as it is withdrawn from around the interventional device. Although this phenomenon may occur on some occasions with non-coated, non-covered, or shorter interventional devices, it is more pronounced with the coated, covered, or longer diameter devices that exert increased deployment forces on the interior wall of the sheath. With such coated, covered, or longer diameter devices, the stretching of the sheath causes the distance between adjacent turns of the coil to increase. This longitudinal expansion of the reinforcing coil adversely affects the ability of the sheath wall to withstand the radial expansive forces exerted on the interior of the wall by the stent, which can result in the formation of pockets along the wall of the sheath between adjacent coil turns. When this occurs, surfaces of the undeployed stent may expand into such pockets, thereby undesirably increasing the resistance imparted by the stent upon the sheath, and hindering efficient deployment of the stent. In addition, the sheath may elongate as it is withdrawn from the stent. When such elongation occurs, the distance the sheath handle travels is reduced, which may prevent the stent from being fully deployed in the vessel from the sheath.

It is desired to provide an improved introducer sheath or other medical apparatus suitable for traversing tortuous passageways in the patient's anatomy during deployment of a medical interventional device, such as an expandable stent. More particularly, it is desired to provide an improved introducer sheath that is capable of efficiently deploying interventional devices that exert high radial forces on the sheath during deployment.

SUMMARY

The problems of the prior art are addressed by the introducer sheath of the present invention. In one form thereof, the introducer sheath includes an inner liner having a passageway extending longitudinally therethrough. A reinforcing member comprising a coil having adjacent coil turns is positioned longitudinally over the inner liner. Each coil turn has a cross-section comprising opposing end portions and a center portion, wherein a thickness of the coil turns at the end portions is greater than a thickness at the center portion. An outer jacket is positioned longitudinally over the inner liner and the coil, and is bonded to the inner liner between the coil turns.

In another form thereof, the invention comprises an introducer sheath. The introducer sheath includes an inner liner having a passageway extending longitudinally therethrough. A coil having adjacent coil turns is positioned longitudinally over the inner liner. Each of the coil turns has a cross-section comprising opposing end portions, and a center portion disposed between the opposing end portions. The center portion has a thickness not exceeding about one-third of a thickness of the end portions for reducing a bending modulus of the coil, and the end portions have a generally curved outer surface. An outer jacket is positioned longitudinally over the inner liner and the coil. The outer jacket is bonded to the inner liner between the coil turns. At least a distal end portion of the outer jacket has a durometer between about 70 and 90 on the Shore D scale.

In still another form thereof, the invention comprises a method for forming an introducer sheath. An inner liner is positioned over a mandrel. A coil having adjacent coil turns is positioned longitudinally over the inner liner. Each of the coil turns has a cross-section comprising opposing end portions and a center portion disposed between the opposing end portions, wherein the end portions have a greater thickness than a thickness of the center portion. A polymeric outer jacket is positioned longitudinally over the inner liner and the coil. An assembly comprising the mandrel, inner liner, reinforcing member and outer jacket is exposed to sufficient heat to at least partially melt the outer jacket such that a melted portion of said outer jacket flows between the coil turns and bonds to an outer surface of the inner liner.

DETAILED DESCRIPTION OF THE DRAWINGS AND THE PRESENTLY PREFERRED EMBODIMENTS

Figure 1:
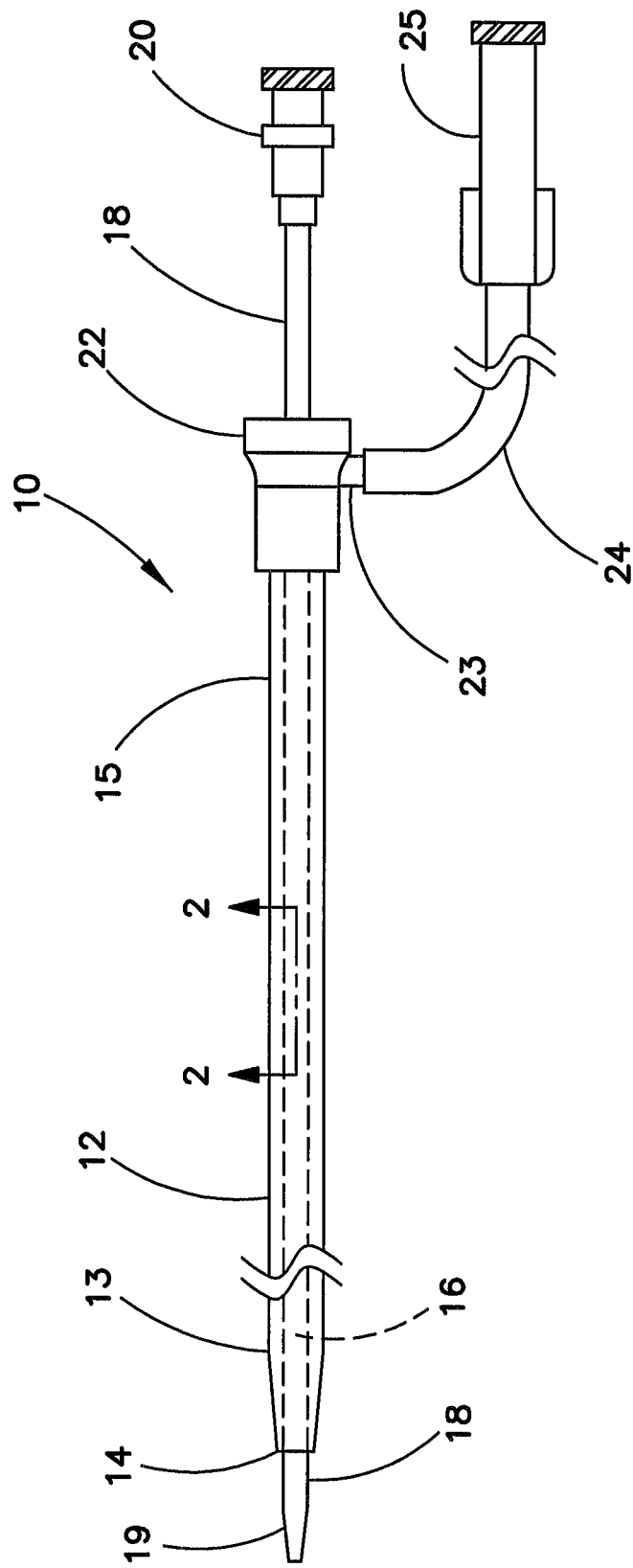
FIG. 1 is a side view of an introducer sheath according to an embodiment of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the sheath, as well as the axial ends of component features of the sheath. The term "proximal" is used in its conventional sense to refer to the end of the sheath (or component thereof) that is closest to the operator during use of the device. The term "distal" is used in its conventional sense to refer to the end of the sheath (or component thereof) that is initially inserted into the patient, or that is closest to the patient during use.

When conventional introducer sheaths are used to deploy medical interventional devices, such as stents, having a relatively short length, such deployments may often be carried out without undue complication. Typically, the stent is nested, or housed, in the distal portion of the sheath in a radially compressed condition. As the stent is deployed from the distal end of the sheath, the stent radially expands to the diameter of the body passageway in which it has been positioned. The relatively short length of the stent, most of which are less than about 80 mm in length, typically provides minimal resistance to the interior of the sheath as the compressed sheath is deployed therefrom.

When comparatively longer stents (e.g., stents greater than about 100 mm in length, and especially, stents greater than about 140 mm in length) are deployed from prior art sheaths, however, the deployment of the stent from a sheath may be less than optimal. Due to the greater length of these stents, a greater aggregate outward force is exerted by the compressed stent upon the interior wall of the sheath, when compared to the force exerted by a stent of a lesser length. As a result, a higher push force must typically be imparted by the inner catheter to overcome the tendency of the stent to remain with the sheath as the sheath is withdrawn from the passageway. A high push force as described may also be required upon deployment of coated or covered stents of any length from the sheath. This is due to the increased forces exerted against the wall of the sheath by the larger diameter coated or covered stent when compared to an otherwise similar, but uncoated or uncovered stent.

The forces exerted by the compressed stent upon the interior wall of the sheath upon deployment may cause the sheath to stretch, or elongate, in the longitudinal direction as the sheath is withdrawn from around the stent. Stretching may have little practical significance when smaller stents are positioned within the sheath. However, as stated above, such stretching can become problematic with larger stents and/or with coated or covered stents, such that in some cases, the stent cannot be efficiently deployed from the elongated sheath.

One way to address the problem of elongation of the sheath is to increase the stiffness of the outer jacket material of the sheath. A sheath having a stiffer outer jacket has less propensity to stretch upon deployment of the stent when compared to one having a more flexible outer jacket. As a result, the likelihood of deployment difficulties is minimized.

Although the use of the stiffer outer jacket addresses the problem of sheath elongation as described, the flexibility of the overall sheath is compromised when compared to an otherwise similar sheath having a more flexible outer jacket. In addition, when the stiff sheath also includes a flat wire coil, the sheath has an increased likelihood of cracking upon bending as the sheath traverses a curved passageway in the body of the patient. This increased likelihood of cracking is believed due, at least in part, to the presence of the defined edges present at each of the corners of the flat wire coil, and to the concentration of mass at the interior center of the flat wire.

FIG. 1 illustrates a side view of an introducer sheath 10 according to an embodiment of the present invention. Introducer sheath 10 includes an outer tube 12, having a distal portion 13 and a proximal portion 15. Preferably, distal portion 13 tapers to a tapered distal end 14. An inner passageway 16 extends through sheath 10 in well-known fashion.

In FIG. 1, sheath 10 is shown in combination with an optional dilator, or inner catheter, 18 and a connector hub 22. Dilators, inner catheters, and connector hubs for use with introducer devices, such as sheath 10, are well known in the art, and the elements illustrated in FIG. 1 may be replaced with various other elements known in the art. As shown herein, inner catheter 18 extends longitudinally through the passageway of the sheath. The inner catheter includes a tapered distal end 19 for accessing and dilating an access site, typically over a wire guide (not shown), by any conventional access technique, such as the well-known Seldinger technique. A Luer lock connector 20 may be attached at the proximal end of the inner catheter for connection to a syringe or other medical apparatus in well-known fashion.

Optional connector hub 22 is attached about the proximal end of the sheath during use. Connector hub 22 may include one or more conventional valve members, such as disk valves (not shown), for preventing the backflow of fluids therethrough. Connector hub 22 may also include a side arm 23, to which a polymeric tube 24 and a conventional connector 25 may be connected for introducing and aspirating fluids therethrough in well-known fashion.

Figure 2:
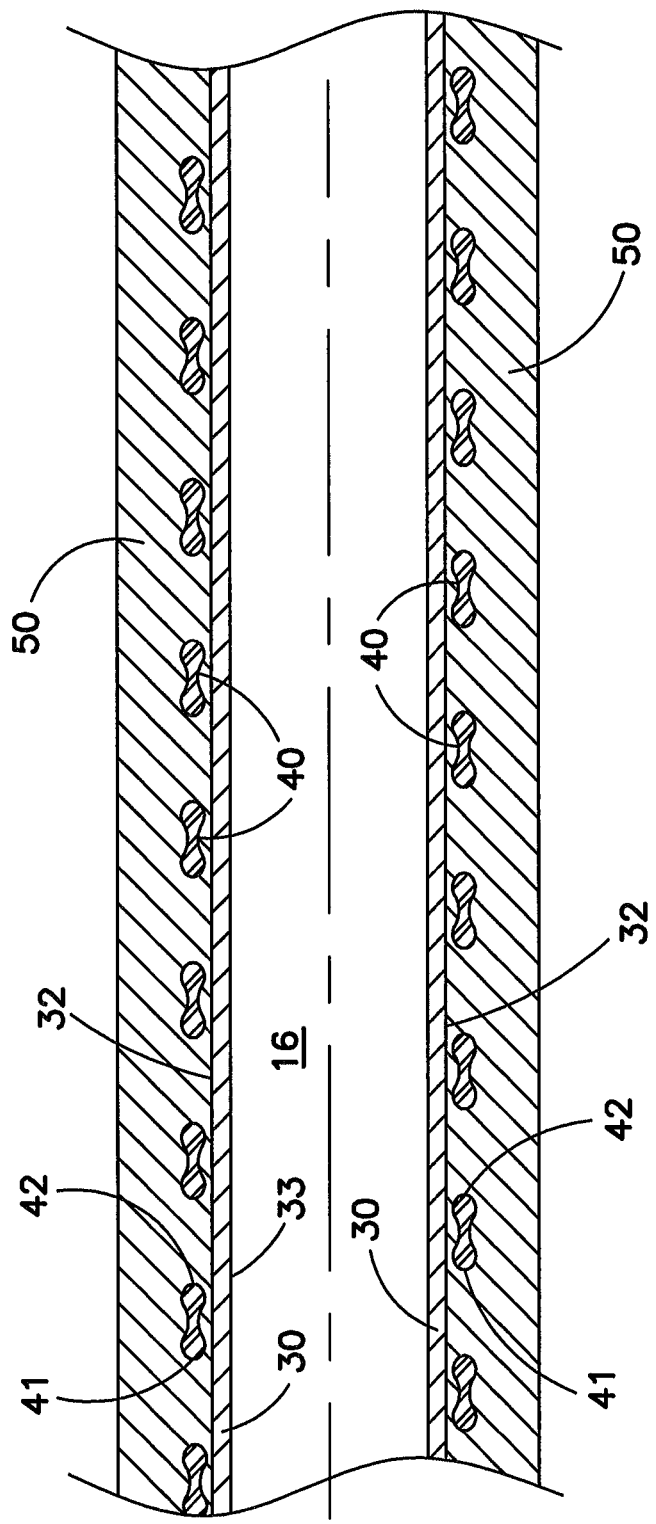
FIG. 2 is a longitudinal cross-sectional view of a segment of the introducer sheath, taken along line 2-2 of FIG. 1.

FIG. 2 is an enlarged longitudinal cross-sectional view of a segment of introducer sheath 10 of FIG. 1. This figure illustrates the layered structure of the sheath wall. The view of introducer sheath 10 depicted in FIG. 2 does not include the optional inner catheter 18 disposed in passageway 16, as shown in FIG. 1. As illustrated, sheath 10 comprises an inner liner 30, having a radially outer surface 32 and a radially inner surface 33. A reinforcing member, i.e., coil 40, is wound or otherwise fitted around outer surface 32 of the inner liner. A polymeric outer layer or jacket 50 is bonded to the outer surface 32 of inner liner 30 through the spaced turns of the coil 40. The cross-sectional profile of coil 40 is further described hereinbelow.

Inner liner 30 is typically formed of a lubricious material. Preferably, the lubricious material comprises a fluoropolymer, such as PTFE or FEP. Lubricious liners for sheaths are well known in the medical arts, and those skilled in the art can readily select an appropriate liner for a particular use. The lubricious material provides a slippery, low friction inner surface 33 to ease insertion and/or withdrawal through passageway 16 of the inner catheter and/or a medical interventional device, such as a stent. Inner liner 30 preferably has a substantially uniform inner diameter that extends the entire length of passageway 16, to allow passage therethrough of an interventional device having the largest possible diameter. The radially outer surface 32 of liner 30 may be roughened in any conventional manner, such as by machine grinding or chemical etching, to form an irregular surface to facilitate bonding with outer jacket 50. The wall of the liner will also preferably have sufficient structural integrity to prevent the outer jacket and/or coil turns from protruding into inner passageway 16.

Outer jacket 50 may generally be formed from any composition commonly used for such purposes in a medical device. Preferably, outer jacket 50 comprises a heat formable polymeric material capable of forming a secure bond with inner liner 30, and more preferably, with a roughened outer surface 32 of the liner. Non-limiting examples of suitable compositions include a polyether block amide, a polyamide (nylon), a polyurethane, and like compositions capable of securely bonding, adhering, or otherwise securely engaging inner liner 30. In many cases it is preferred to form outer jacket 50 from a material having a lower melt temperature than that of liner 30. To this end, the outer jacket can be heated at a temperature suitable to melt the jacket to facilitate bonding with the inner liner. When the heat formable material melts, portions flow between the respective turns of the coil, and bond to the outer surface 33 of the inner liner.

The outer jacket composition is formulated to have a durometer that provides sufficient flexibility to enable the sheath to bend through the desired body pathway. In some instances, the outer jacket may have a durometer of a range commonly provided in sheaths used to deploy medical interventional devices. One very common durometer range that may be suitable in many such instances is about 55 to 65 on the Shore D scale. However, as stated above, in order to address problems such as sheath elongation that may be encountered upon deployment of an elongated interventional device and/or a coated or covered interventional device, it may be desirable to utilize an outer jacket formed of a composition having a higher durometer, or in other words, that is stiffer than a jacket formulated to have the conventional durometer range described above.

One particular outer jacket composition that may be utilized with the profiled reinforcing member described herein is a composition having a durometer between about 70 and 100 on the Shore D scale. Preferably, the durometer is between about 70 and 90, and more preferably about 80 on the Shore D scale. Such a composition provides an outer jacket having a greater stiffness than commonly provided in such sheaths. When a conventional sheath of a type described above having an outer jacket durometer between about 55 and 65 on the Shore D scale is utilized to deploy a stent or other interventional device that has a greater length and/or outer diameter than normal, the distal portion of the sheath having the stent nested therein may have insufficient radial rigidity to adequately withstand the outwardly-directed forces exerted by the compressed stent on the interior wall of the sheath.

By increasing the stiffness (i.e., durometer) of at least the distal portion of the outer jacket, that is, the portion of the sheath that houses the stent, this sheath portion has a greater ability to withstand the radially outwardly-directed forces exerted by the stent, when compared to a sheath having a more flexible distal portion. Although other portions of the sheath outer jacket may also be formed from a high durometer material as described above, it is desired that at least the distal portion of the sheath that houses the stent (e.g., the distal-most 1-30 cm of the sheath) have such durometer.

The reinforcing member, such as coil 40, of sheath 10 may be formed from materials known for such use in the medical arts. Non-limiting examples of such materials include metals, metal alloys (e.g., stainless steel or a shape memory composition such as nitinol), and composite materials. If desired, the coil 40 may extend the entire length of sheath 10. However, it is generally preferred that the coil terminate short of the proximal and distal ends of the sheath in well-known fashion. Terminating the coil short of the distal end facilitates the ability to form a desired configuration (e.g., a distal taper) at the non-reinforced distal end. Terminating short of the proximal end facilitates flaring of that end.

Figure 3A:
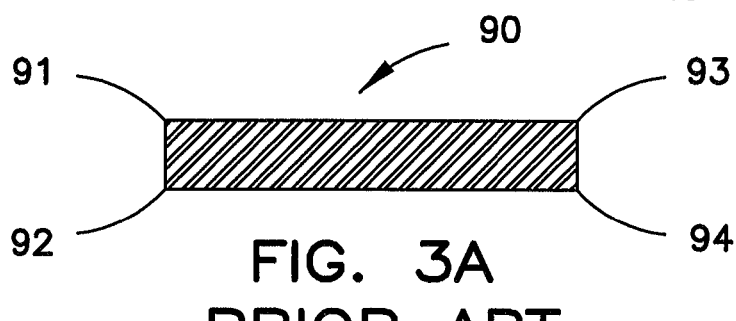
FIG. 3A is a cross-sectional view of a coil turn from the prior art sheath of FIG. 3, removed from the remaining elements of the sheath.
Figure 3:
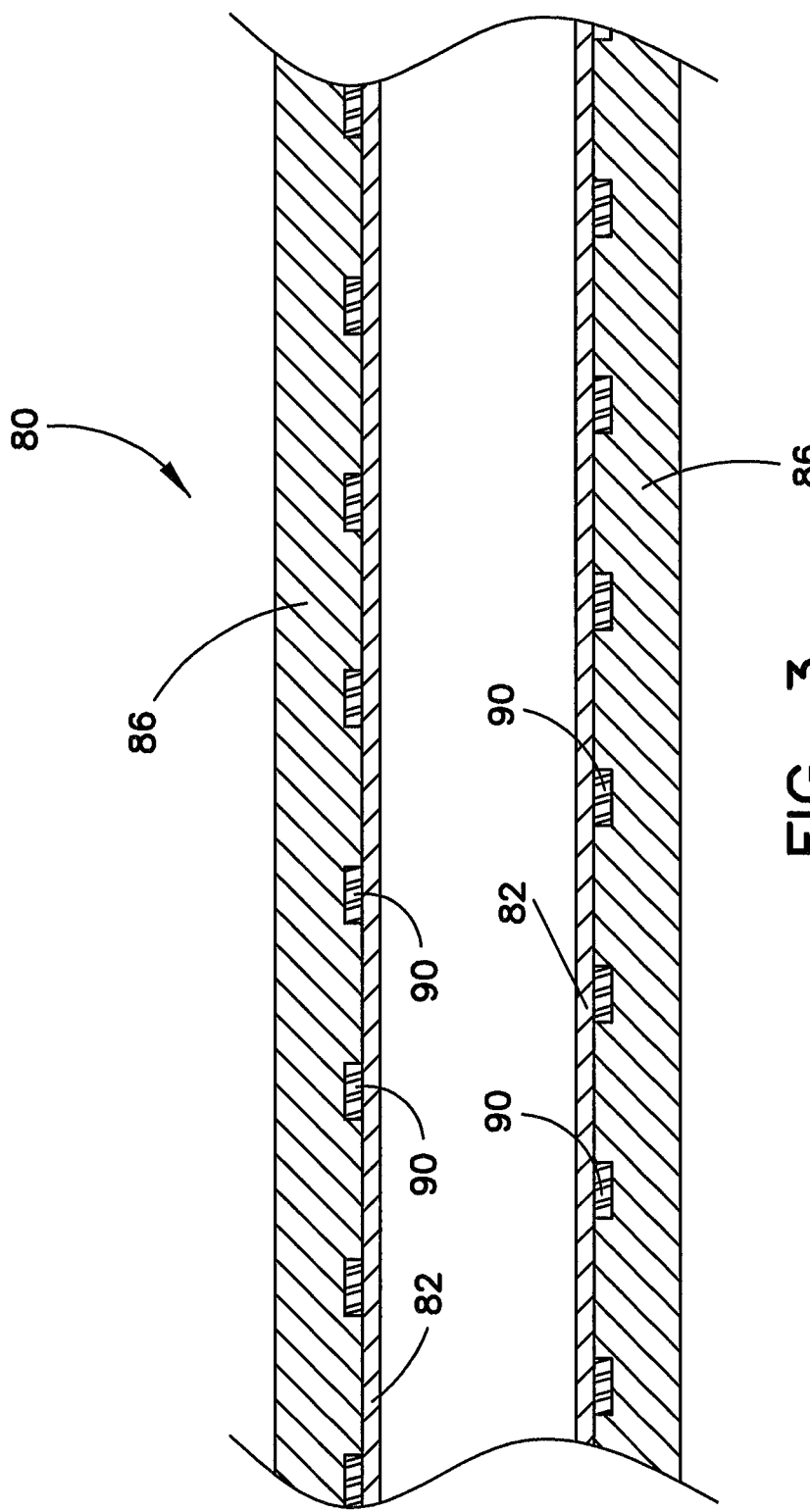
FIG. 3 is a longitudinal cross-sectional view of a prior art sheath.

Conventionally, the reinforcing coil of an introducer sheath was formed from flat wire having a generally rectangular cross-section. See, e.g., FIGS. 3 and 3A. FIG. 3 illustrates a prior art sheath 80 having flat wire coil 90. Sheath 80 includes an inner liner 82 and an outer jacket 86 as before. Flat wire coil 90 has a rectangular cross-section, and includes four squared edges 91, 92, 93, 94, as best shown in FIG. 3A. Providing a sheath having a flat wire coil enables the sheath to maintain the smallest possible wall diameter, while at the same time providing suitable radial support to the sheath.

With a sheath having a conventional outer jacket durometer, e.g., about 55-65 or less on the Shore D scale, the sheath having a flat wire coil is generally able to bend about most body pathways without cracking. However, when it is desired to provide a sheath having an outer jacket of a higher durometer (e.g., 70 to 90 or higher on the Shore D scale) than provided in the more conventional sheaths, the stiffer outer jacket material has an increased propensity to crack upon bending of the sheath.

Figure 2A:
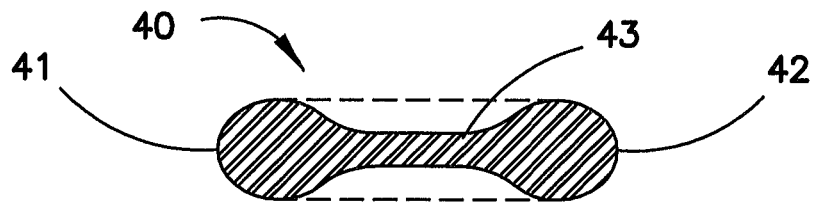
FIG. 2A is a cross-sectional view of a coil turn from the sheath of FIG. 2, removed from the remaining elements of the sheath.
Figure 2B:
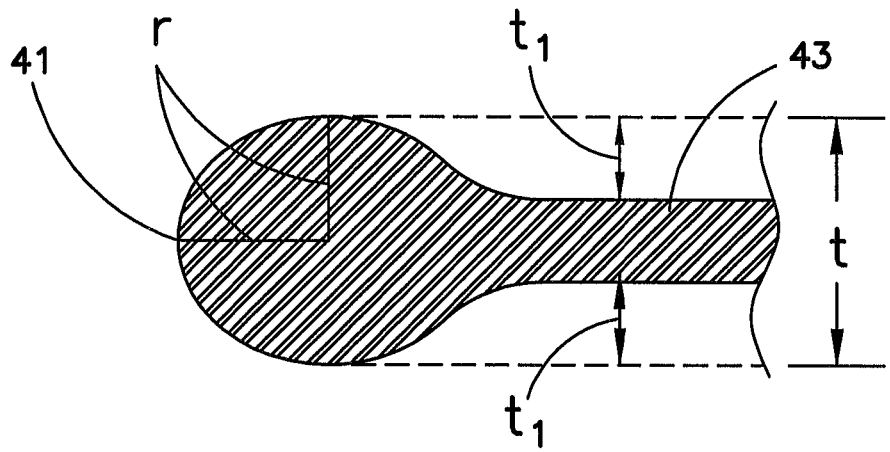
FIG. 2B is an enlarged view of coil end 41 of FIG. 2A.

The coil utilized in the sheath described herein is configured in a manner to reduce the likelihood that the outer jacket of the sheath will crack upon bending. One form of a coil 40 utilized in sheath 10 is illustrated in FIGS. 2, 2A, and 2B. As shown in the figures, the mass at the center portion 43 of the wire cross section is reduced when compared to conventional flat wire of the type shown in FIGS. 3, 3A. The dotted lines in FIGS. 2A, 2B are provided to mimic the mass that would otherwise be present at the center portion of a conventional flat wire. Reducing the thickness at the center of the wire cross section when compared to the end portions decreases the bending modulus of the wire. This improves the overall flexibility of the wire, and therefore, of the sheath. If the overall thickness of the entire wire was reduced, rather than the center portion as described, the radial support provided by the coil would be adversely affected. By maintaining the mass at the end portions 41, 42 as described, the coil provides a suitable level of radial support to the sheath, notwithstanding the reduced thickness at the center portion.

Those skilled in the art will appreciate that varying amounts of mass may be reduced in a particular application. In some applications wherein maximum sheath flexibility may not be required, lesser amounts of mass may be removed when compared to an application in which maximal sheath flexibility is desired. In general, as the thickness of the area removed increases, there is an increase in flexibility of the sheath. Optimally, the amount of mass removed would approach one-half of the thickness "t" of the wire, leaving only a sufficient amount of mass to connect the two wire ends 41, 42. Generally, it is preferred to remove up to about one-third ("$t_1$") of the thickness of the wire from either surface of the wire (FIG. 2B). This is believed in most applications to impart a sufficient decrease in the bending modulus of the wire to provide suitable wire flexibility, while at the same time maintaining structural integrity of the wire. Those skilled in the art will appreciate that in some applications somewhat greater amounts, e.g., up to about 40-45%, of the thickness of the wire from each surface may be removed to provide maximal bending. Similarly, in instances in which less bending is expected, lesser amounts of wire, e.g., between about 10 and 30%, may be removed from each surface.

Although it is preferred to remove equal amounts of mass from each surface as described and as shown in the figures, this may not be required in all instances. Thus, in some applications, different amounts of mass may be removed from the respective upper and lower surfaces of the wire. As a further alternative, in some applications, suitable bending may be achieved by removing mass from only one surface of the wire, and leaving the other surface intact.

In addition to removing mass from the center portion of the wire as described, it is preferred to provide a reinforcing wire having curved, or rounded, wire ends. See, e.g., wire ends 41, 42, in FIGS. 2, 2A, 2B. By rounding the outer edges of the wire, the stress concentrations at the wire edges are reduced when compared to the stress concentrations at the edges of a conventional flat wire coil, such as squared edges 91-94 of conventional flat wire coil 90. Reducing the stress concentration at the edges of a wire further reduces the likelihood that the sheath will crack along one or more edges upon bending, or kinking, of the sheath as it traverses a curved body pathway. One way to quantify an amount of curvature in a preferred arrangement is described by the formula "$r=t/2$", wherein "r" is the radius of the coil end (e.g., end 41 or 42) and "t" is the thickness of the wire (FIG. 2B). Although an amount of curvature defined by the formula recited above is preferred for most applications, the skilled artisan may determine that a lesser amount of curvature (e.g., $r=t/4$, $r=t/8$, or $r=t/16$) may be suitable for a particular application. Those skilled in the art will recognize that as the denominator increases, the radius at the edges is decreasing. It is believed that a skilled artisan can readily determine a suitable degree of curvature for a particular application when applying the teachings of the present disclosure.

Although coil 40 as shown in the figures includes the preferred arrangement of both rounded edges and a reduced mass center portion, the presence of rounded edges may not be required in all embodiments. Rather, the decrease in bending modulus provided by the reduced mass center portion may in some instances improve the flexibility of the sheath to such an extent that rounding of the edges is unnecessary. However, it is believed preferable to include both rounded edges and a reduced mass center portion. In this instance, the artisan need not separately consider whether the presence of sharp edges is adverse to the functioning of the sheath in the particular application. Furthermore, it simplifies manufacturing techniques to construct such sheaths from a common wire configuration.

Figure 2C:
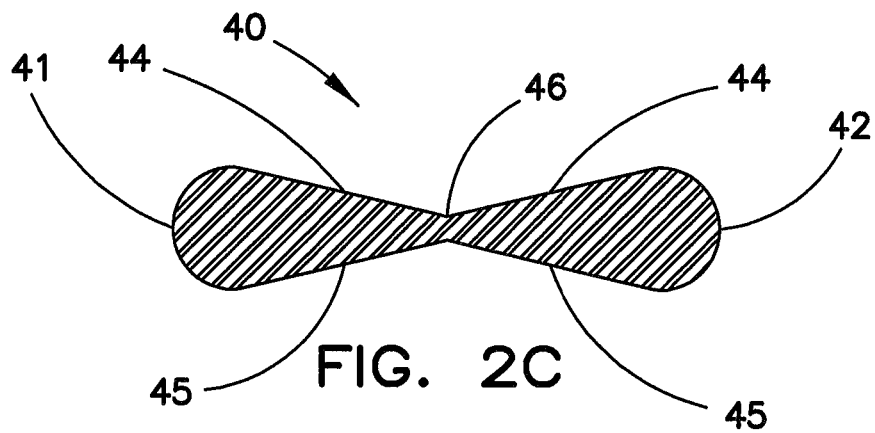
FIG. 2C is a cross-sectional view of an alternative coil turn profile.

The cross-sectional profile of the coil need not be exactly as shown in FIG. 2A. As stated, it is desired to reduce the mass at the center of the wire. Those skilled in the art recognize that other profiles would accomplish the objective of minimizing the amount of mass at the center of the wire. FIG. 2C illustrates one example of an alternative cross-sectional profile. In this case, relatively straight lines 44, 45 extend from coil ends 41, 42 and meet at a center portion 46. Other wire configurations may be substituted for those shown in FIGS. 2A and 2C, as long as sufficient mass is removed from the center of the wire to decrease the bending modulus of the wire such that the overall flexibility of the wire, and therefore, of the sheath, is enhanced. Although a certain amount of trial and error can be employed to determine suitable dimensions and configurations for a wire that is profiled in the general manner described herein, the skilled artisan can readily create such a wire when proceeding in accordance with the teachings provided herein.

Those skilled in the art will appreciate that the profile of the reinforcing member and/or the stiffness of an outer jacket composition may vary in a particular sheath depending upon factors such as the body pathway to be traversed, and the length and/or diameter of the interventional device to be deployed from the sheath. It is believed that a skilled artisan can readily determine a suitable combination of factors to achieve a sufficient amount of flexibility of the sheath for a particular application when applying the teachings provided herein.

Coils having a profile as described herein may be readily prepared by known techniques. For example, a conventional flat wire can be drawn through a die having the desired configuration. Alternatively, round wire can be drawn down through a series of well-known steps to impart the desired profile in the wire. Once a wire having the desired profile is formed, the wire may then be coiled using a conventional coiling machine in the same fashion as flat wire is presently coiled in a sheath of the type described herein.

One method of forming the sheath 10 will now be described. Initially, the inner liner 30 is positioned along a suitably-sized mandrel. Generally, the mandrel will have an outer diameter substantially the same as the inner diameter of the inner liner to insure a close tolerance between the two. The profiled coil 40 is then positioned over the inner liner and mandrel by any conventional technique, and the tubular outer jacket 50 is positioned over the mandrel, liner and coil. The entire assembly is placed in a suitable heat shrink enclosure. Heat shrink enclosures for use in forming medical devices are well known in the art. Fluorinated ethylene propylene (FEP) is a particularly preferred composition for use herein as a heat shrink enclosure. Those skilled in the art will appreciate that various alternative compositions for the heat shrink enclosure are also suitable for use in forming this sheath, as long as the melt temperature of the material used for the outer jacket is lower than that of the heat shrink enclosure.

The heat shrink enclosure and contents are placed in an oven and baked (typically at about 385° F. (196° C.) when FEP is used as the heat shrink and a polyether block amide is used as an outer jacket material) for a suitable period of time to melt the outer jacket material such that it flows between the coil turns as described and bonds with the outer surface of the inner liner. After removal from the oven, the entire assembly is cooled, the FEP enclosure is cut away, and the mandrel is removed.

Additional details of the construction or composition of the various elements of sheath 10 not otherwise disclosed are not believed to be critical to the present invention, so long as the recited elements possess the strength and/or physical properties to enable them to perform as required. Many such details not described herein are recited in detail in the incorporated-by-reference U.S. Pat. No. 5,380,304, and U.S. Patent Publication No. 2001/0034514.

It is therefore intended that the foregoing detailed description be regarded as illustrative rather than limiting, and that it be understood that it is the following claims, including all equivalents, that are intended to define the spirit and scope of this invention.

The invention claimed is:

1. An introducer sheath comprising:
   an inner liner having a passageway extending longitudinally therethrough;
   a reinforcing member positioned longitudinally over the inner liner, the reinforcing member comprising a coil having adjacent coil turns, each of said coil turns having a monolithic cross-section comprising opposing end portions and a center portion, wherein a thickness of said coil turns at said end portions is greater than a thickness at said center portion, wherein said thickness of said center portion does not exceed about one-third of said thickness of said end portions; and
   an outer jacket positioned longitudinally over said inner liner and said coil, said outer jacket bonded to said inner liner between said coil turns.

2. The introducer sheath of claim 1, wherein at least a distal end portion of the outer jacket has a durometer between about 70 and 90 on the Shore D scale.

3. The introducer sheath of claim 1, wherein said coil turn cross-section has an upper and lower surface, and wherein up to about 40% of said coil turn thickness is removed from said center portion at each of said upper and lower surfaces when compared to the thickness of said end portions.

4. The introducer sheath of claim 1, wherein said coil turn cross-section has an upper and lower surface, and wherein between about 10 and 30% of said coil turn thickness is removed from said center portion of at least one of said upper and lower surfaces.

5. The introducer sheath of claim 1, wherein said end portions have a generally curved outer surface.

6. The introducer sheath of claim 5, wherein at least one of said coil end portions has a radius r and a thickness t, said end portion generally curved surface being defined by the formula $r=t/2$.

7. The introducer sheath of claim 5, wherein at least one of said coil end portions has a radius r and a thickness t, said end portion generally curved outer surface not exceeding $r=t/4$.

8. The introducer sheath of claim 1, wherein at least a distal end portion of the outer jacket has a durometer between about 70 and 90 on the Shore D scale, wherein the thickness of the center portion is about one-third of the thickness of the end portions, and wherein said end portions have a generally curved outer surface.

9. The introducer sheath of claim 1, wherein the thickness of the center portion is about one-third of the thickness of the end portions.

10. The introducer sheath of claim 1, wherein said inner liner comprises a lubricious fluoropolymer, and said outer jacket comprises at least one of a polyether block amide, a polyamide, and a polyurethane.

11. An introducer sheath comprising:
    an inner liner having a passageway extending longitudinally therethrough, said inner liner having an outer surface;
    a coil positioned longitudinally over the inner liner, the coil having adjacent coil turns, each of said coil turns having a monolithic cross-section comprising opposing end portions and a center portion disposed between said opposing end portions, said center portion having a thickness not exceeding about one-third of a thickness of said end portions for reducing a bending modulus of said coil, said end portions having a generally curved outer surface, at least one of the coil end portions having a radius r and a thickness t such that the generally curved outer surface is defined by the formula $r=t/2$; and
    an outer jacket positioned longitudinally over said inner liner and said coil, said outer jacket bonded to said inner liner between said coil turns, at least a distal end portion of the outer jacket having a durometer between about 70 and 90 on the Shore D scale.

12. The introducer sheath of claim 11, wherein at least one of said coil end portions has a radius r and a thickness t, said end portion generally curved outer surface not exceeding $r=t/4$.

13. The introducer sheath of claim 11, wherein said said thickness of said center portion is about one-third of said thickness of said end portions.

* * * * *